(12) United States Patent
Tofighbakhsh (10) Patent No.: US 10,163,314 B2
(45) Date of Patent: Dec. 25, 2018

(54) PROGRAMMABLE DEVICES TO GENERATE ALERTS BASED UPON DETECTION OF PHYSICAL OBJECTS

(71) Applicant: AT&T Intellectual Property I, L.P., Atlanta, GA (US)

(72) Inventor: Mostafa Tofighbakhsh, Cupertino, CA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

(21) Appl. No.: 15/203,061

(22) Filed: Jul. 6, 2016

(65) Prior Publication Data

US 2018/0012469 A1   Jan. 11, 2018

(51) Int. Cl.

| | |
|---|---|
| *G08B 21/02* | (2006.01) |
| *H04B 1/3827* | (2015.01) |
| *H04W 4/70* | (2018.01) |
| *H04W 4/90* | (2018.01) |
| *G08B 13/196* | (2006.01) |
| *G08B 25/08* | (2006.01) |
| *G08B 25/10* | (2006.01) |
| *A61B 5/00* | (2006.01) |

(52) U.S. Cl.
CPC ....... *G08B 21/02* (2013.01); *G08B 13/19602* (2013.01); *G08B 25/08* (2013.01); *G08B 25/10* (2013.01); *H04B 1/385* (2013.01); *H04W 4/70* (2018.02); *H04W 4/90* (2018.02); *A61B 5/486* (2013.01)

(58) Field of Classification Search
CPC .............. G08B 21/02; G08B 13/19613; G08B 13/19656; G08B 13/19671; G08B 25/08; G08B 25/10; G08B 13/19602; G06F 19/345; G06F 19/3431; H04W 4/70; H04W 4/90
See application file for complete search history.

(56) References Cited

U.S. PATENT DOCUMENTS

| | | | |
|---|---|---|---|
| 6,535,131 B1 * | 3/2003 | Bar-Shalom | A01K 11/008 340/573.1 |
| 6,611,206 B2 | 8/2003 | Eshelman et al. | |
| 6,706,002 B1 | 3/2004 | Halleck et al. | |
| 6,720,880 B2 * | 4/2004 | Gutta | G08B 13/19602 340/573.4 |
| 7,319,780 B2 * | 1/2008 | Fedorovskaya | G06F 19/321 128/922 |
| 8,500,635 B2 | 8/2013 | Zilca et al. | |
| 8,659,657 B2 | 2/2014 | Brumfield et al. | |
| 9,101,263 B2 | 8/2015 | Jung et al. | |
| 9,173,567 B2 | 11/2015 | Jain et al. | |
| 9,189,599 B2 | 11/2015 | Adler et al. | |
| 2005/0154264 A1 | 7/2005 | Lecompte et al. | |

(Continued)

*Primary Examiner* — Adnan Aziz (57) ABSTRACT

A device, computer-readable medium, and method for performing a remedial action in response to detecting a presence of an object are disclosed. For example, a processor may receive a configuration file, the configuration file identifying an object, an alert, and a remedial action, detect a presence of the object, wherein the object is a triggering object relating to a mental condition of a user, send the alert to a monitoring device, in response to detecting the presence of the object, and perform the remedial action, in response to detecting the presence of the object.

20 Claims, 3 Drawing Sheets

(56) References Cited

U.S. PATENT DOCUMENTS

| | | | |
|---|---|---|---|
| 2005/0228236 A1 | 10/2005 | Diederich et al. | |
| 2007/0173733 A1* | 7/2007 | Le | G16H 40/63 600/544 |
| 2009/0124920 A1* | 5/2009 | Patterson | A61B 5/0482 600/544 |
| 2009/0189983 A1* | 7/2009 | Brumfield | G08B 13/19613 348/159 |
| 2012/0038462 A1* | 2/2012 | Adler | H04Q 9/00 340/10.1 |
| 2012/0290215 A1* | 11/2012 | Adler | G06F 19/3431 702/19 |
| 2013/0076528 A1 | 3/2013 | Boettner et al. | |
| 2013/0184517 A1 | 7/2013 | Collier | |
| 2013/0245396 A1* | 9/2013 | Berman | G06F 19/3418 600/301 |
| 2014/0023999 A1* | 1/2014 | Greder | A61B 5/0482 434/236 |
| 2014/0143064 A1* | 5/2014 | Tran | A61B 5/0022 705/14.66 |
| 2014/0336473 A1* | 11/2014 | Greco | A61B 5/486 600/301 |
| 2015/0223731 A1* | 8/2015 | Sahin | A61B 5/16 600/301 |
| 2015/0254955 A1* | 9/2015 | Fields | G08B 21/02 705/4 |
| 2015/0265217 A1 | 9/2015 | Fenders et al. | |
| 2016/0001781 A1* | 1/2016 | Fung | G06F 19/345 701/36 |
| 2016/0037292 A1 | 2/2016 | King | |
| 2016/0143534 A1* | 5/2016 | Hyde | A61B 5/11 600/553 |
| 2016/0189517 A1* | 6/2016 | Weast | G08B 21/02 340/573.1 |

* cited by examiner

PROGRAMMABLE DEVICES TO GENERATE ALERTS BASED UPON DETECTION OF PHYSICAL OBJECTS

The present disclosure relates generally to detecting alert conditions at endpoint devices, e.g., within a cellular network environment, and more particular to devices, computer-readable media, and methods for detecting physical objects near endpoint devices, and for generating alerts and performing remedial actions based upon the detection of such physical objects.

BACKGROUND

Wearable sensor devices are popular for use as everyday exercise accessories and may also be used in managed care settings. For instance, wearable sensors, such as pedometers, heart rate monitors, and the like may be used in conjunction with an application to determine the general health of a subject, the performance of the subject during an activity, and so forth. However, these wearable devices may be limited to the applications for which they are designed and may have limited adaptability to the unique situations of different users or subjects.

SUMMARY

In one example, the present disclosure discloses a device, computer-readable medium, and method for performing a remedial action in response to detecting a presence of an object. For example, a processor may receive a configuration file, the configuration file identifying an object, an alert, and a remedial action, detect a presence of the object, wherein the object is a triggering object relating to a mental condition of a user, send the alert to a monitoring device, in response to detecting the presence of the object, and perform the remedial action, in response to detecting the presence of the object.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses methods, computer-readable media, and devices for performing a remedial action in response to detecting a presence of an object. For example, certain individuals may have "mental" conditions that relate to particular physical objects, such as a type of animal, a particular other person, or an inanimate object, such as a bridge, a tunnel, a building, such as a doctor's office, vehicles, such as planes, trains, or fire engines, and so forth. As referred to herein, these types of objects may be referred to as "triggering objects" insofar as the presence of such objects may cause an emotional response to a user having a mental condition related to any one of such objects. A "mental" condition could be a clinical condition, but it does not need to be a clinical condition. Broadly, a "mental" condition relates to a user's emotional response to a particular type of object, e.g., a fear response, a distress response, an apprehension response, an anger response, a paralysis response, and the like.

To illustrate, a child may have a fear of bears. Thus, even at a zoo where most others would feel entirely safe viewing a bear in a closed habitat, the child may still have great distress. In another example, a user may be a generally responsible driver. However, a fear of bridges or tunnels may cause distress to the user, and may cause erratic driving as a secondary result. In one example, the present disclosure provides for the detection of a presence of an object, e.g., a triggering object, in the vicinity of an endpoint device of a user, and for the sending of an alert to a monitoring device and the performing of a remedial action in response to the detection of the presence of the object. In one example, the presence of the object may be detected using a camera of the endpoint device of the user.

For instance, a configuration file may be created under the direction of a parent, a physician, such as a psychiatrist, or other caregiver. The configuration file may include a sample image of a trigger object. In one example, the sample image may be provided by the caregiver or may be provided by the user. In another example, the caregiver may provide a text-based or speech-based input, where the sample image may be retrieved from an image repository based upon the input. The configuration file may also include parameters set by a caregiver for an alert to be sent to a monitoring device in response to a detection of the presence of the object. For instance, the caregiver may set his or her own endpoint device to receive alerts, may set another monitoring device to receive alerts and/or to collect statistics regarding multiple alerts, and so on. In addition, the configuration file may also include parameters set by a caregiver for a remedial action to be performed in response to a detection of the presence of the object. For instance, the remedial action may comprise playing calming music, presenting a message for the user to address the condition, and the like. In one example, the remedial action may comprise sending a further alert to emergency response entity. For instance, a call may be placed to 911, to a medical provider that specializes in mental health treatment, or the like.

In one example, the configuration file may be to configure the endpoint device of a user to detect a presence of an object near the endpoint device, to send an alert, and to perform a remedial action. In another example, a configuration file may be to configure a network-based server to detect the presence of an object, e.g., near an endpoint device of a user, and/or to generate an alert and to perform a remedial action in response to detecting the presence of the object. For instance, an endpoint device may collect images via a camera of the endpoint device and upload the images to the network-based server. The network-based server may then compare the images to a sample image of the object, whereupon, when the object is detected in one or more of the images based upon the sample image, the network-based server may send the alert to the monitoring device and perform the remedial action. In such an example, the remedial action may comprise sending an additional alert to an emergency response entity. Alternatively, or in addition, the remedial action may comprise sending an instruction to the endpoint device, e.g., to play calming music, to present a message for the user to address the condition, e.g., to present a reminder of coping techniques to the user, to place an automatic call connecting the endpoint device to a telephone or other endpoint device of a caregiver, and so forth.

In one example, the presence of an object may be further verified by using global positioning system (GPS) readings or other location information. For instance, certain objects may have fixed locations, such as bridges, tunnels, schools, fire stations, and so forth. As such, in one example, an endpoint device or a network-based server performing operations in accordance with a configuration file may further make reference to electronic map data, in conjunction with location information of the endpoint device, to determine the presence of an object. For example, the presence of the object may be determined when both an image captured via a camera of the endpoint device is found to include the object, and when location information of the endpoint device is indicative that the endpoint device is at or near a known location of the object. In one example, "near" may be defined based upon a selection of the caregiver or may be pre-set for multiple users of a service in accordance with the present disclosure. For example, near may be defined to be within 500 feet if the endpoint device is moving at a walking speed, running speed, or less, but may be defined to be one mile or greater if the endpoint device is found to be moving at motor vehicle speed, e.g., 25 miles per hour or greater. However, in examples where location information is not used to verify the presence of the object as determined via a camera of an endpoint device, "near" may be considered to be any distance at which the camera of the device is able to capture an image that includes the object and in which the object is detectable in the image based upon a comparison to a sample image of the object.

In one example, the presence of an object may be further verified by using audio or video data. For example, the camera of an endpoint device may also be used to capture video data. Similarly, a microphone of the endpoint device may be used to capture audio data from the environment around the endpoint device. In addition, an audio sample and/or a video sample relating to the object may also be provided during the creation of the configuration file. For instance, an audio sample may include a bear growling, speech of a person, sounds of a car or an airplane engine, and so forth. A video sample may reveal a gait or other mannerism of a person or an animal, for example. Accordingly, audio or video captured at the endpoint device may be compared to the sample audio or sample video. For instance, the endpoint device or a network based device may implement a pattern matching algorithm to determine if the captured audio matches the audio sample or to determine if a gait or other mannerism of a person (e.g., a clown at a circus or a mascot at a sports event) or animal in a captured video matches that of the subject in a video sample. If so, it may be further verified that the object is present.

In another example, the sending of an alert and/or the performance of a remedial action may also be qualified by the detection of a physiological state of a user. For instance, a user may be progressing out of a condition relating to an object. As such, the presence of the object may sometimes still cause distress to the user, while at other times the presence of the object may no longer elicit a response from the user. Accordingly, in one example the sending of an alert and/or the performing of a remedial action may be suppressed if there is no adverse response detected in the user. However, if it is detected that the state of the user is agitated, distressed, or the like, when the presence of a triggering object is also detected, then the alert may be sent and/or the remedial action be performed. To illustrate, the endpoint device may include or may be in communication with a physiological sensor, such as a heart rate monitor, a blood pressure monitor, or the like. In another example, the device may comprise or may be in communication with a wearable eyeglass-based computing device that is capable of measuring pupil dilation, a level of forehead sweat, and so forth. Thus, various thresholds for physiological measurements from one or more of such sensors may be set in a configuration file. If a threshold is reached, it may be determined that the state of the user warrants an alert and remedial action, e.g., if the presence of the object is also determined.

Thus, the present disclosure provides for personalized monitoring to detect when alerts should be sent and remedial actions should be performed. In particular, a caregiver may select parameters for a configuration file to be provided to a network-based device or to an endpoint device of the user such that the caregiver may receive an alert and provide a personalized remedial action for the user, e.g., in response to detecting the presence of a triggering object which relates to a condition of the user. These and other aspects of the present disclosure are discussed in greater detail below in connection with the examples of FIGS. 1-3.

Figure 1:
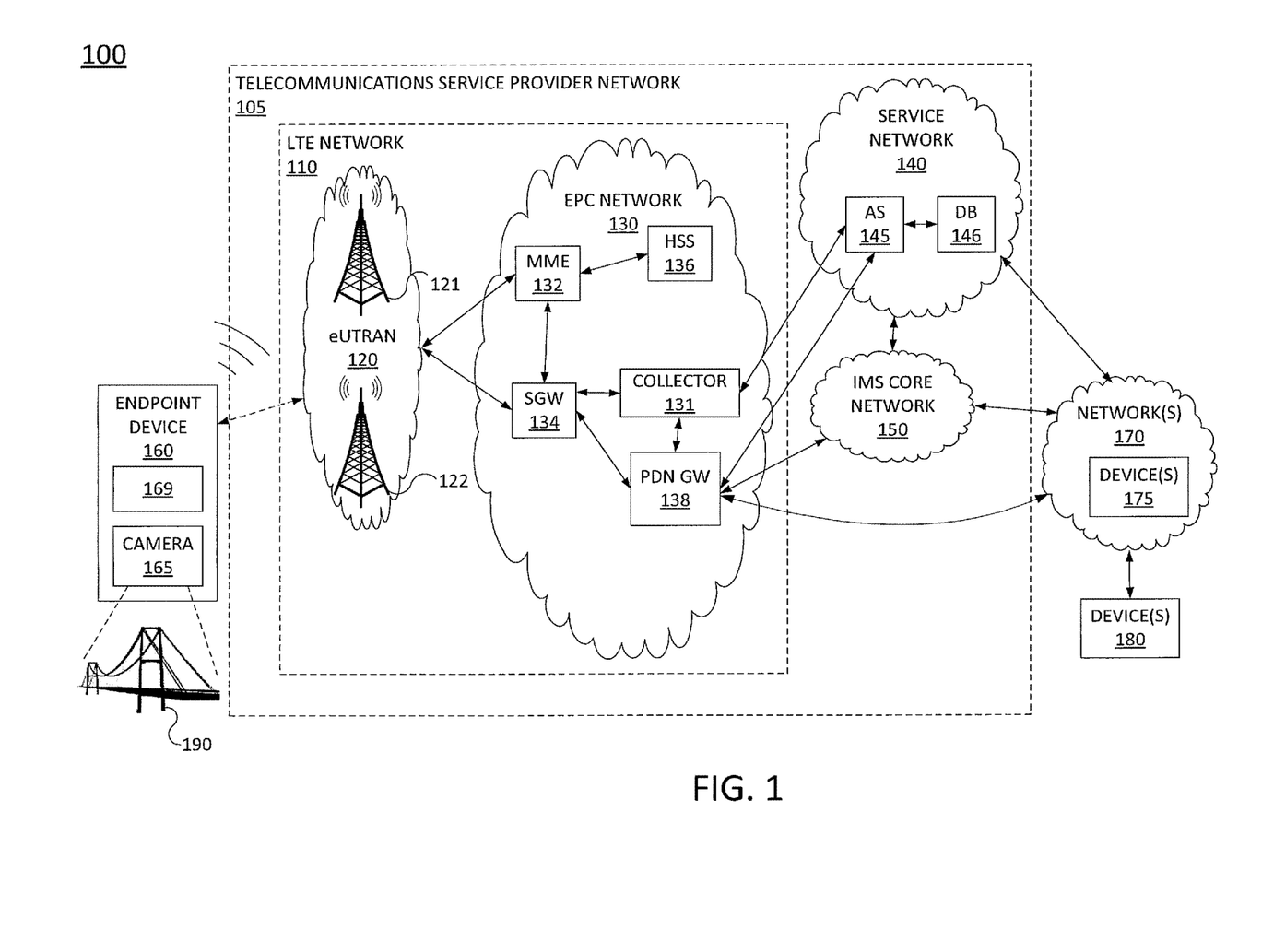
FIG. 1 illustrates an example system related to the present disclosure.

To better understand the present disclosure, FIG. 1 illustrates an example network, or system 100 that may implement embodiments of the present disclosure for performing a remedial action in response to detecting a presence of an object. In one example, the system 100 includes a telecommunications service provider network 105. The telecommunications service provider network 105 may comprise a Long Term Evolution (LTE) network 110, a service network 140, and a core network, e.g., an IP Multimedia Subsystem (IMS) core network 150. The system 100 may further include other networks 170 connected to the telecommunications service provider network 105. As shown in FIG. 1, the system 100 may connect endpoint device 160 with application server (AS) 145 in service network 140, with devices 175 in networks 170, with other endpoint devices (not shown) and/or with other components of telecommunication service provider network 105. The endpoint device 160 may comprise a cellular telephone, a smartphone, a tablet computing device, a laptop computer, a pair of computing glasses, a wireless and/or cellular enabled wristwatch, or any other wireless and/or cellular-capable mobile telephony and computing device (broadly, a "mobile endpoint device"). As illustrated in FIG. 1, endpoint device 160 may include a camera 165 for capturing images and/or video, e.g., of an object 190. For instance, as illustrated in FIG. 1, in one example object 190 may comprise a bridge. In one example, endpoint device may further include a module 169. In one example, module 169 may comprise a global positioning system (GPS) module or the like, for detecting a location of the endpoint device 160. In one example, module 169 may comprise a microphone for capturing audio data. Alternatively, or in addition, module 169 may comprise one or more physiological sensors for detecting a state of a user of the endpoint device 160.

Although module 169 is illustrated as being a part of endpoint device 160, in another example, module 169 may comprise a separate device that is in communication with endpoint device 160. For instance endpoint device 160 may comprise a smartphone, while module 169 may comprise a heart rate monitor that measures a user's heart rate and communicates wirelessly with the endpoint device 160, e.g., using Institute of Electrical and Electronics Engineers (IEEE) 802.11 based communications (e.g., "Wi-Fi"), IEEE 802.15 based communications (e.g., "Bluetooth", "ZigBee", etc.), or the like.

In one example, the LTE network 110 comprises an access network and a core network. For example, as illustrated in FIG. 1, LTE network 110 may comprise an evolved Universal Terrestrial Radio Access Network (eUTRAN) 120 and an evolved packet core (EPC) network 130. The eUTRANs are the air interfaces of the 3$^{rd}$ Generation Partnership Project (3GPP) LTE specifications for mobile networks. In one example, EPC network 130 provides various functions that support wireless services in the LTE environment. In one example, EPC network 130 is an Internet Protocol (IP) packet core network that supports both real-time and non-real-time service delivery across a LTE network, e.g., as specified by the 3GPP standards. In one example, all eNodeBs, e.g., including eNodeBs 121 and 122 in the eUTRAN 120, are in communication with the EPC network 130. In operation, LTE user equipment or user endpoints (UE), such as endpoint device 160, may access wireless services via the eNodeBs 121 and 122 located in eUTRAN 120. It should be noted that any number of eNodeBs can be deployed in an eUTRAN.

In EPC network 130, network devices Mobility Management Entity (MME) 132 and Serving Gateway (SGW) 134 support various functions as part of the LTE network 110. For example, MME 132 is the control node for the LTE access networks, e.g., including eUTRAN 120. In one embodiment, MME 132 is responsible for user equipment tracking and paging (e.g., such as retransmissions), bearer activation and deactivation process, selection of the SGW, e.g., SGW 134, and user authentication. In one embodiment, SGW 134 routes and forwards user data packets, while also acting as the mobility anchor for the user plane during inter-eNodeB handovers and as the anchor for mobility between LTE and other wireless technologies, such as 2G and 3G wireless networks.

In addition, EPC (common backbone) network 130 may comprise a Home Subscriber Server (HSS) 136 that contains subscription-related information (e.g., subscriber profiles), performs authentication and authorization of a wireless service user, and provides information about the subscriber's location. The EPC network 130 may also comprise a packet data network (PDN) gateway 138 which serves as a gateway that provides access between the EPC network 130 and various data networks, e.g., service network 140, IMS core network 150, networks 170, and the like. The packet data network gateway 138 is also referred to as a PDN gateway, a PDN GW or a PGW.

In one example, service network 140 may comprise one or more devices, such as application server (AS) 145 for providing services to subscribers, customers, and or users. For example, telecommunications service provider network 105 may provide a cloud storage service, web server hosting, and other services. As such, service network 140 may represent aspects of telecommunications service provider network 105 where infrastructure for supporting such services may be deployed. In one example, endpoint device 160 may be connected to service network 140 and/or AS 145 via PDN GW 138, and/or via PDN GW 138 and IMS core network 150. In one example, AS 145 may comprise a computing system, such as computing system 300 depicted in FIG. 3, specifically configured to provide one or more functions for performing a remedial action in response to detecting a presence of an object, in accordance with the present disclosure. For instance, telecommunications service provider network 105 may provide a service via AS 145 for subscribers, e.g., caregivers, to configure endpoint devices and/or AS 145 detect a presence of an object, and to send alerts and perform remedial actions in response to the detection of an object. Although a single application server, AS 145, is illustrated in service network 140, it should be understood that service network 140 may include any number of components to support one or more services that may be provided to one or more subscribers, customers, or users by the telecommunications service provider network 105. In one example, service network 140 may also include a database (DB) 146, e.g., a physical storage device integrated with AS 145, or attached or coupled to the AS 145, to store configuration files, electronic map data, global positioning system (GPS) data, captured images, audio data, or video data, measurements of a user state via physiological sensors, or other data in accordance with the present disclosure.

In one example, networks 170 may represent one or more enterprise networks, a circuit switched network (e.g., a public switched telephone network (PSTN)), a cable network, a digital subscriber line (DSL) network, a metropolitan area network (MAN), an Internet service provider (ISP) network, and the like. In one example, the other networks 170 may include different types of networks. In another example, the other networks 170 may be the same type of network. Devices 175 may include server hardware, personal computers, desktop computers, laptop computers, personal digital assistants (PDAs), tablet computing devices, circuit-switched or packet communications-based telephones, or any other wireless and/or wired communication enabled computing device. In one example, networks 170 may represent the Internet in general. In one example, endpoint device 160 may be connected to one of devices 175 via PDN GW 138, and/or via PDN GW 138 and IMS core network 150.

In one example, one of the devices 175 may comprise a server for providing a service to configure endpoint devices and/or the one of the devices 175 to detect a presence of an object, and to send alerts and perform remedial actions in response to the detection of an object. For instance, one of the devices 175 may be provided by a third-party to enable caregivers or others to generate configuration files to be deployed on endpoint devices or within the one of the devices 175 to perform various functions, in accordance with the present disclosure. Accordingly, in one example, the one of the devices 175 may comprise a computing system, such as computing system 300 depicted in FIG. 3, specifically configured to provide one or more functions for performing a remedial action in response to detecting a presence of an object, in accordance with the present disclosure.

In one example, a caregiver may utilize a computing device, e.g., one of the devices 180, to connect to a server (e.g., one of the devices 175 or AS 145) that provides a service to configure an endpoint device and/or a network-based device with a configuration file, in accordance with the present disclosure. For illustrative purposes, an example where one of the devices 180 connects to AS 145 is described. In particular, AS 145 may provide an interface where a caregiver may input various parameters for creating a configuration file in accordance with the present disclosure. For instance, AS 145 may provide an interactive application in the form of hypertext markup language (HTML) web pages, client-side extensible markup language (XML), Java, or Python forms, and the like, or in the form of an interactive voice response (IVR) system, to the one of the devices 180. Devices 180 may comprise personal computers, desktop computers, laptop computers, personal digital assistants (PDAs), tablet computing devices, circuit-switched or packet communications-based telephones, or any other wireless and/or wired communication enabled computing device. In accordance with the application, the one of the devices 180 may present dialog boxes, menus, and the like for the caregiver to enter and/or to select various parameters. In other words, the caregiver may provide inputs via one of the devices 180 which may be transmitted to AS 145. AS 145 may receive such inputs, send responses to the one of the devices 180, and process such inputs into a configuration file.

To illustrate, the caregiver may provide a telephone number, user identification code, or other identifier of an endpoint device of a user under the care of the caregiver. The caregiver may provide a sample image of an object, and may further provide sample audio and/or sample video, depending upon the nature of the object. In one example, the caregiver may provide map/location data regarding fixed locations of an object, e.g., if the object is a home, a school, a bridge, a tunnel, or other object with a fixed location that is known to the caregiver. The caregiver may also select one or more monitoring devices and/or recipients for receiving alerts when the presence of the object is detected near the endpoint device. For example, the monitoring devices and/or recipients may be specified by telephone numbers, email addresses, usernames for a chat application, etc. The caregiver may further specify remedial actions to be performed when the presence of the object near the endpoint device is detected. For example, the caregiver may specify that an additional alert should be sent to an emergency response entity, may provide a sample of calming music that should be played at the endpoint device, may provide a message for the user to address the condition in visual or audio form to be presented at the endpoint device, and so forth.

In one example, the caregiver may also select one or more physiological parameters indicative of a state of a user that may be used to determine whether an alert should be sent and/or a remedial action be performed. AS 145 may therefore receive such inputs and process such inputs into a configuration file for an endpoint device and/or for AS 145. For example, AS 145 may create a configuration file and transmit the configuration file to endpoint device 160. Endpoint device 160, when configured, or programmed with the configuration file may then detect a presence of an object near the endpoint device 160, and send an alert and perform a remedial action in accordance with the configuration file. In another example, AS 145 may send instructions to endpoint device 160 to collect and send certain categories of data, e.g., images, video, audio, location and/or physiological sensor data to AS 145, which AS 145 may then process in accordance with the configuration file to detect a presence of an object near the endpoint device 160, and to send an alert and perform a remedial action in accordance with the configuration file.

In one example, system 100 may also include a collector 131 in EPC network 130. In one example, collector 131 may comprise a computing system, such as computing system 300 depicted in FIG. 3. For instance, collector 131 may comprise a server to receive instructions from AS 145, to interact with and configure gateways and/or other network elements components within EPC network 130 in response to such instructions, and/or to perform other operations in accordance with the present disclosure. In one example, collector 131 may interface with various elements within EPC network 130, such as SGW 134, and PDN GW 138 to collect image data, video data, audio data, location data, physiological sensor data, or other data from endpoint devices connected to access networks of the LTE network 110, such as endpoint device 160 connected to eUTRAN 120, which may then be compiled and sent to AS 145 or one of the devices 175 for further processing based upon various configuration files, in accordance with the present disclosure.

It should be noted that the system 100 has been simplified. In other words, the system 100 may be implemented in a different form than that illustrated in FIG. 1. For example, the system 100 may be expanded to include additional networks, such as network operations center (NOC) networks, additional eUTRANs, and so forth. The system 100 may also be expanded to include additional network elements such as border elements, routers, switches, policy servers, security devices, gateways, a content distribution network (CDN) and the like, without altering the scope of the present disclosure. In addition, system 100 may be altered to omit various elements, substitute elements for devices that perform the same or similar functions, combine elements that are illustrated as separate devices, and/or implement network elements as functions that are spread across several devices that operate collectively as the respective network elements. For example, various elements of eUTRAN 120, EPC network 130, service network 140, and IMS core network 150 are omitted for clarity, including gateways or border elements providing connectivity between such networks, internal routers within EPC network 130, and so on. Similarly, due to the relatively large number of connections available between devices in the system 100, various links between MME 132, SGW 134, eNodeBs 111 and 112, controller 131, PDN GW 138, AS 145, and other components of system 100 are also omitted for clarity.

In addition, although aspects of the present disclosure have been discussed above in the context of a long term evolution (LTE)-based network, examples of the present disclosure are not so limited. For example, the teachings of the present disclosure can be applied to other types of wireless networks (e.g., a 2G network, a 3G network, and the like, or a future technology or standard-based network). Similarly, although the AS 145 and DB 146 are illustrated as components of service network 140, and collector 131 is illustrated as a component within EPC network 130, in other examples, any one or more of these components may be deployed in a different configuration. For example, collector 131 may reside within service network 140 and may communicate with components in EPC network 130 via PDN GW 138, for example. In another example, the AS 145 and collector 131 may be combined into a single component within EPC network 130 or in service network 140. Furthermore, although only a single AS 145 and DB 146 are illustrated in FIG. 1, in other, further, and different examples, more examples of any one or more of these components may be deployed within the system 100. Thus, these and other modifications are all contemplated within the scope of the present disclosure.

Figure 2:
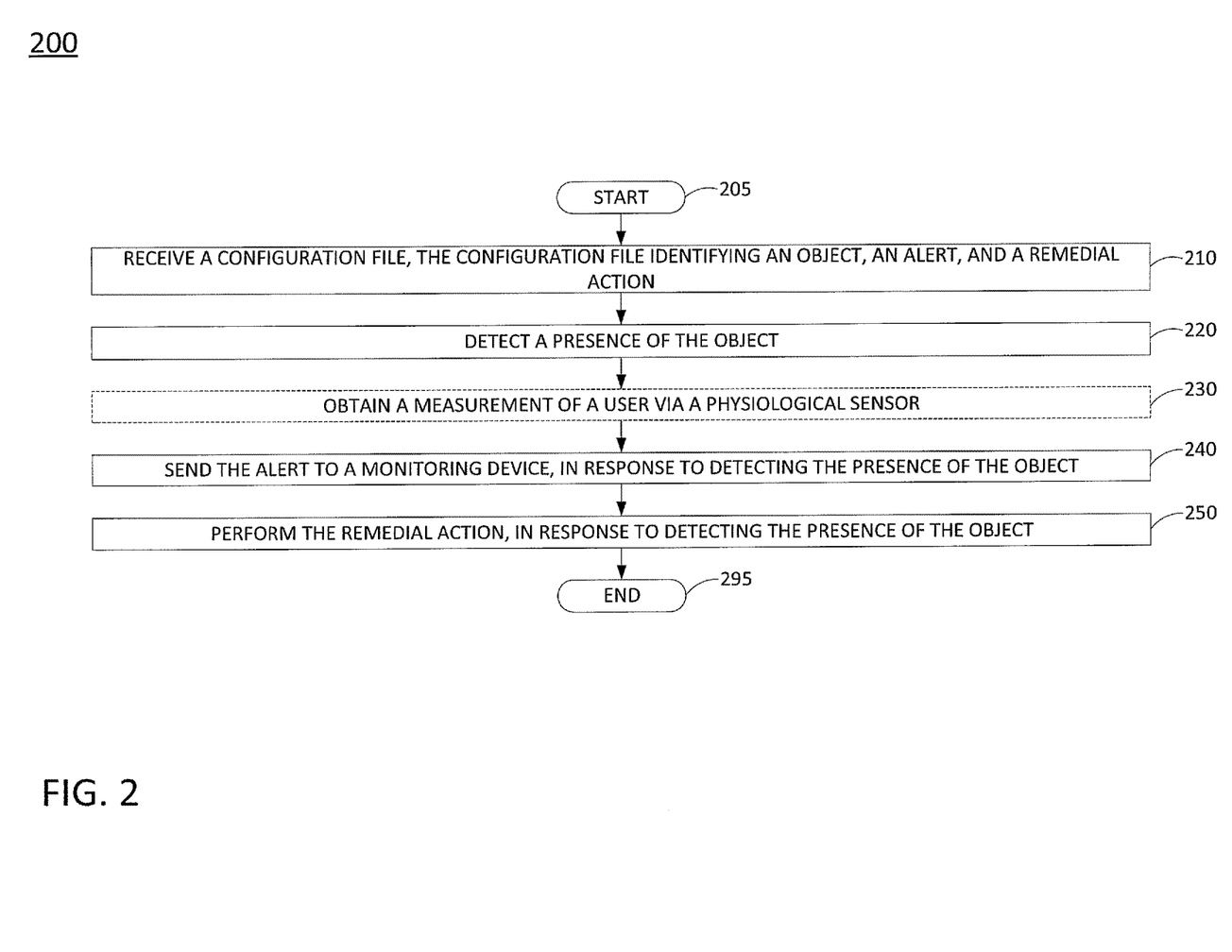
FIG. 2 illustrates a flowchart of an example method for performing a remedial action in response to detecting a presence of an object.

FIG. 2 illustrates a flowchart of an example method 200 for performing a remedial action in response to detecting a presence of an object, in accordance with the present disclosure. In one example, steps, functions and/or operations of the method 200 may be performed by a network-based device, such as one of the devices 175, application server (AS) 145 or AS 145 in conjunction with other components of the system 100, such as collector 131 and/or endpoint device 160, and so forth. In another example, the method 200 may be performed by an endpoint device, such as endpoint device 160. In one example, the steps, functions, or operations of method 200 may be performed by a computing device or system 300, and/or processor 302 as described in connection with FIG. 3 below. For instance, computing device or system 300 may represent an application server, or an endpoint device of the present disclosure. For illustrative purposes, the method 300 is described in greater detail below in connection with an example performed by a processor, such as processor 302. The method 200 begins in step 205 and proceeds to step 210.

At step 210, the processor receives a configuration file that identifies an object, an alert, and a remedial action. In one example, the object may comprise a trigger object that relates to a mental condition of a user, e.g., an object that may cause distress to the user. In one example, the object may be particularly distressing to the user as an individual, for any number of reasons, but may not be a general cause for distress to a majority of people. In one example, the configuration file may be for an endpoint device. For example, the processor may be a processor deployed in an endpoint device of a user under the care of a caregiver that has provided input parameters for the configuration file. In another example, the processor may be a processor deployed in a network-based device. In such an example, the configuration file may further identify an endpoint device of the user to which the configuration file applies.

In one example, the alert may identify a monitoring device for receiving the alert when the presence of the object is detected near the endpoint device. In one example, the alert may identify a plurality of monitoring devices. The monitoring devices may be specified by telephone numbers, email addresses, and the like. The alert may take the form of an automated voice call, a voice message, an email, a text message, and so forth. In one example, the remedial action may comprise playing calming music, presenting a message for the user to address the condition, and the like. In one example, the remedial action may comprise sending a further alert to an emergency response entity. For instance, a call may be placed to 911, to a medical provider that specializes in mental health treatment, or the like. In one example, the alert may comprise one of a plurality of alerts and the remedial action may comprise one of a plurality of remedial actions. For instance, a text alert may be for sending to one or more recipients, while an audio message alert may be for sending to one or more other recipients. The various recipients may comprise multiple caregivers, such as parents, grandparents, different staff members of a medical provider entity, and so forth. In one example, the configuration file may further include sample audio and/or sample video, map/location data regarding fixed location(s) of an object, and/or one or more physiological parameters indicative of a state of a user that may be used to determine whether the alert should be sent and/or the remedial action be performed.

At step 220, the processor detects a presence of the object. For instance, an image may be obtained from a camera of an endpoint device. For example, the processor may be deployed within the endpoint device, or may be deployed in a network-based device that is in communication with the endpoint device. In either case, the processor may use any number of image recognition or image matching techniques to compare the image obtained via the camera to the sample image to determine that the image obtained via the camera includes the object. In one example, when the image matching/image recognition indicates the object is found in the image obtained via the camera, the presence of the object may be detected. In one example, the processor may be deployed in a network-based device, e.g., in a cellular network while the detecting the presence of the object is performed via an endpoint device. For instance, the processor deployed in the cellular network or the monitoring device may transmit instructions to the endpoint device to: obtain an image via a camera of the endpoint device, determine the presence of the object by comparing a sample image of the object to the image obtained via the camera, e.g., where the image obtained via the camera includes the object, and send a notification to the device, when the presence of the object is determined by the endpoint device.

In one example, the presence of an object may be further verified at step 220 by using audio or video data, as described above. For instance, audio or video captured at the endpoint device may be compared to sample audio or sample video in the configuration file. For instance, the processor may implement a pattern matching algorithm to determine if a captured audio matches the audio sample or to determine if a gait or other mannerism of a person or animal in a captured video matches that of a subject in a video sample. If so, it may be further verified that the object is present. In other words, the presence of the object may be detected at step 220 when the object is found in the image obtained via the camera and when an audio or video captured via the endpoint device also matches an audio sample or a video sample in the configuration file.

Alternatively, or in addition, the presence of an object may be verified by using GPS readings or other location information. For instance, certain object may have fixed locations, such as bridges, tunnels, schools, fire stations, and so forth. As such, in one example, the processor may further make reference to electronic map data, in conjunction with location information of the endpoint device, to determine the presence of an object. In one example, the processor may be deployed in an endpoint device with a GPS module. Accordingly, the processor may compute a location of the endpoint device via the GPS module, and determine that the location is associated with the object based upon the electronic map data. In one example, the electronic map data may be included in the configuration file. In another example, the endpoint device may already possess the electronic map data, which may be used for other applications on the endpoint device. In still another example, the processor may be deployed in a network-based device. In such case, the processor may determine the location of the endpoint device if the endpoint device transmits location readings to the network-based device, or may determine the location of the endpoint device in another way, such as using cellular base station triangulation techniques, or by estimating the location of the endpoint device based upon a received signal strength indicator (RSSI), the serving base station, nearby IEEE 802.11 access points, 802.15 beacons, and so forth. Thus, in one example, the presence of the object may be determined at step 220 when both an image captured via a camera of the endpoint device is found to include the object, and when location information of the endpoint device is indicative that the endpoint device is at or near a location known to include the object.

At optional step 230, the processor obtains a measurement of a user via a physiological sensor. For instance, as mentioned above, the configuration file may include one or more physiological parameters indicative of a state of a user that may be used to determine whether the alert should be sent and/or the remedial action be performed. Accordingly, the endpoint device associated with the configuration file may include or may be in communication with another device that includes a physiological sensor that is capable of generating the measurement of the user regarding the physiological parameter. The physiological sensor may comprise, for example, a heart rate monitor, a blood pressure monitor, and so forth. In one example, optional step 230 may include obtaining a plurality of measurements from one or more sensors. For instance, in one example, a state of the user may be determined from both heart rate and blood pressure measurements.

At step 240, the processor sends the alert to the monitoring device, in response to detecting the presence of the object. For example, as mentioned above, the alert may identify a monitoring device, or a plurality of monitoring devices, for receiving the alert when the presence of the object is detected near the endpoint device. The alert may be sent in the form of an automated voice call, a voice message, an email, a text message, and so forth. In one example, various thresholds for physiological measurements of a user from one or more physiological sensors may be set in the configuration file. Accordingly, in one example, if it is determined that a threshold is reached based upon a measurement or measurements from one or more physiological sensors, it may be determined that the state of the user warrants the alert to be sent, e.g., if the presence of the object is also determined. In other words, the alert is sent when the presence of the object is detected and when a state of the user is detected via the one or more physiological sensors.

At step 250, the processor performs the remedial action, in response to detecting the presence of the object. In one example, the remedial action may comprise playing calming music, presenting a message for the user to address the condition, and the like. In another example, the remedial action may comprise sending a further alert to emergency response entity. In still another example, step 250 may comprise performing a plurality of remedial actions in accordance with the configuration file. As mentioned above, in one example, the processor may be deployed in a network-based device. Thus, in such an example, the remedial action may comprise sending an instruction to the endpoint device of the user. In one example, various thresholds for physiological measurements of a user from one or more physiological sensors may be set in the configuration file. Accordingly, in one example, if it is determined that a threshold is reached based upon a measurement or measurements from one or more physiological sensors, it may be determined that the state of the user warrants the remedial action to be performed, e.g., if the presence of the object is also determined. In other words, the remedial action is performed when the presence of the object is detected and when a state of the user is detected via the one or more physiological sensors.

Following step 250, the method 200 proceeds to step 295. At step 295, the method 200 ends.

In addition, it should be noted that although not specifically specified, one or more steps, functions or operations of the method 200 may include a storing, displaying and/or outputting step as required for a particular application. In other words, any data, records, fields, and/or intermediate results discussed in the method 200 can be stored, displayed and/or outputted to another device as required for a particular application. Furthermore, steps or blocks in FIG. 2 that recite a determining operation or involve a decision do not necessarily require that both branches of the determining operation be practiced. In other words, one of the branches of the determining operation can be deemed as an optional step. It should be noted that the method 200 may be expanded to include additional steps. In addition, one or more steps, blocks, functions, or operations of the above described method 200 may comprise optional steps, or can be combined, separated, and/or performed in a different order from that described above, without departing from the example embodiments of the present disclosure.

As such, the present disclosure provides at least one advancement in the technical field of network-based and/or device-based management of user conditions. In particular, examples of the present disclosure enable loading a configuration file onto an endpoint device or a network-based device to detect the presence of a trigger object, to send an alert to a monitoring device, and to perform a remedial action in response to detecting the presence of the trigger object. For instance, a user may have a mental condition associated with a particular trigger object that may cause unusual emotional response to the user. It should be noted that the triggering objects may be ordinary objects that generally do not elicit such a strong emotional response from the general public, but it does affect a particular user in a negative way. The endpoint device of the user may be configured, e.g., by a medical professional, a parent, or other caregiver to detect the presence of the object, and to provide automated alerts to the caregiver and to automatically perform a remedial action, such as presenting a message for the user to address the condition, playing calming music, and so forth, in response to detecting the presence of the object. Thus, although a medical professional, parent, or other caregiver may not be immediately available to address the condition of the user, an automated remedial action may assist in avoiding greater distress to the user. In addition, examples of the present disclosure improve the functioning of a computing device, e.g., a server or an endpoint device. Namely, servers dedicated to detecting alert conditions are improved in the examples of the present disclosure, such as the application server (AS) described herein, which may manage configuration files for endpoint devices and/or which may receive an image via a camera of an endpoint device, determine the presence of the object by comparing a sample image of the object to the image obtained via the camera, send an alert to a monitoring device, and perform a remedial action in response to detecting the presence of the object, based upon a configuration file. Likewise, endpoint devices are improved to be loaded, e.g., programmed, with a configuration file, and to detect the presence of a trigger object, to send an alert to a monitoring device, and to perform a remedial action according to the configuration file.

Figure 3:
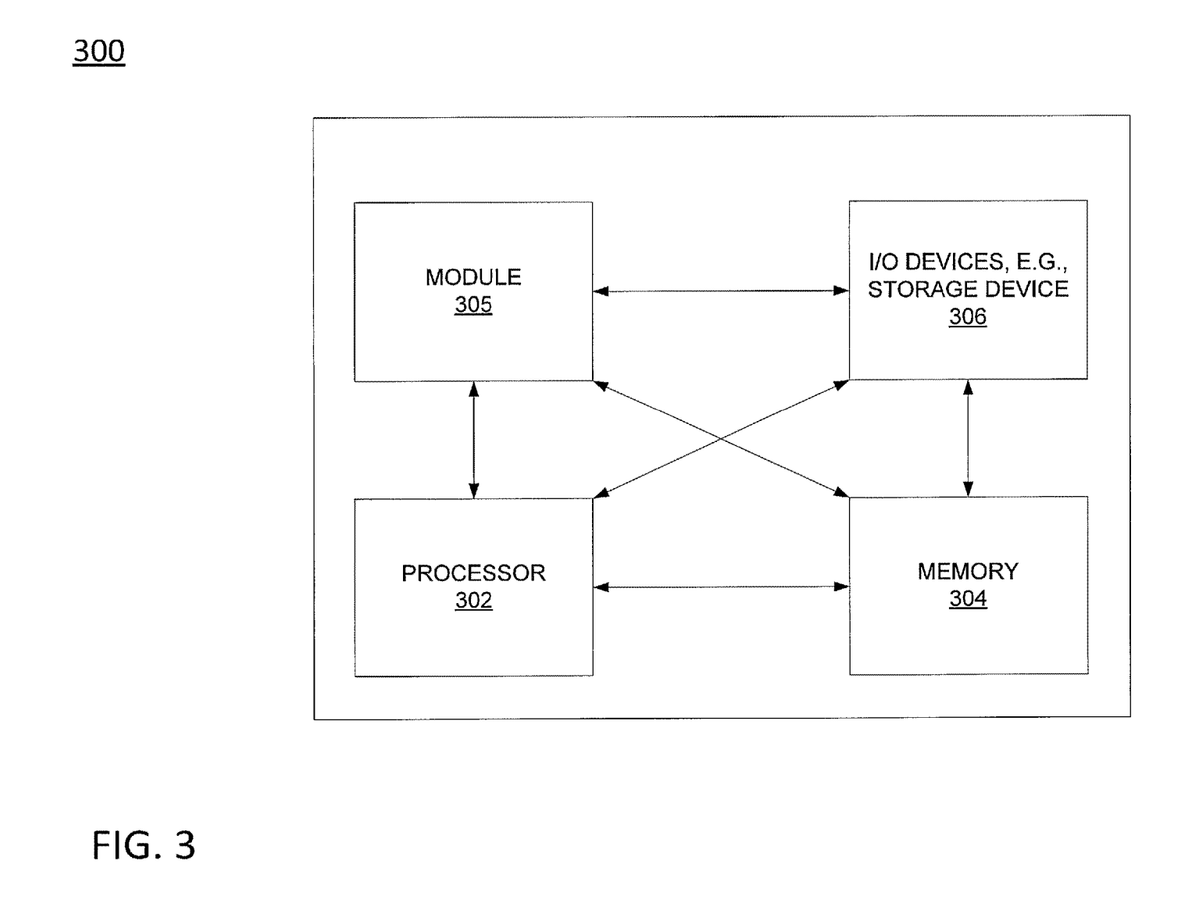
FIG. 3 illustrates an example high-level block diagram of a computer specifically programmed to perform the steps, functions, blocks, and/or operations described herein.

FIG. 3 depicts a high-level block diagram of a computing device suitable for use in performing the functions described herein. As depicted in FIG. 3, the system 300 comprises one or more hardware processor elements 302 (e.g., a central processing unit (CPU), a microprocessor, or a multi-core processor), a memory 304 (e.g., random access memory (RAM) and/or read only memory (ROM)), a module 305 for performing a remedial action in response to detecting a presence of an object, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 200 as discussed above is implemented in a distributed or parallel manner for a particular illustrative example, i.e., the steps of the above method 200, or the entire method 200 is implemented across multiple or parallel computing device, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method 200. In one embodiment, instructions and data for the present module or process 305 for performing a remedial action in response to detecting a presence of an object (e.g., a software program comprising computer-executable instructions) can be loaded into memory 304 and executed by hardware processor element 302 to implement the steps, functions or operations as discussed above in connection with the illustrative method 200. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 305 for performing a remedial action in response to detecting a presence of an object (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A device comprising:
   a processor; and
   a computer-readable medium storing instructions which, when executed by the processor, cause the processor to perform operations, the operations comprising:
   receiving a configuration file, the configuration file identifying a triggering object relating to a mental condition of a user, a threshold for detecting a negative mental state of the user, a type of automated alert, and an automated remedial action;
   detecting a presence of the triggering object;
   obtaining a measurement of the user via a physiological sensor in response to the detecting of the presence of the triggering object;
   detecting the negative mental state of the user, when the measurement of the user via the physiological sensor reaches the threshold for detecting the negative mental state of the user;
   sending an alert of the type of automated alert to a monitoring device, in response to detecting the presence of the triggering object, wherein the alert identifies the negative mental state of the user and a location of the user; and
   performing the automated remedial action, in response to the detecting the presence of the triggering object and the detecting the negative mental state of the user based upon the measurement, wherein the automated remedial action comprises presenting a message to the user to avoid the negative mental state of the user.

2. The device of claim 1, wherein the automated remedial action further comprises:
   sending an additional alert to an emergency response entity.

3. The device of claim 1, wherein the device comprises an endpoint device.

4. The device of claim 3, wherein the device further comprises a camera.

5. The device of claim 4, wherein the configuration file provides a sample image of the triggering object, and wherein the detecting the presence of the triggering object comprises comparing the sample image of the triggering object to an image obtained via the camera that includes the triggering object.

6. The device of claim 5, further comprising:
   a global positioning system module.

7. The device of claim 6, wherein the detecting the presence of the triggering object further comprises computing a location via the global positioning system module, and determining that the location is associated with the triggering object.

8. The device of claim 7, wherein the presence of the triggering object is detected when the image obtained via the camera is determined to include the triggering object, based upon the sample image of the triggering object, and when it is determined that the location is associated with the triggering object.

9. The device of claim 7, wherein the location is associated with the triggering object via electronic map data.

10. The device of claim 3, further comprising:
    the physiological sensor.

11. The device of claim 10, wherein the sending the alert to the monitoring device is in response to the detecting the presence of the triggering object and the detecting the negative mental state of the user based upon the measurement.

12. The device of claim 1, wherein the triggering object comprises:
    a person;
    an animal; or
    an inanimate object.

13. The device of claim 1, wherein the device is deployed in a cellular network.

14. The device of claim 13, wherein the automated remedial action comprises sending an instruction to an endpoint device.

15. The device of claim 13, wherein the detecting the presence of the triggering object is performed via an endpoint device, and wherein the device or the monitoring device transmits instructions to the endpoint device to:
  obtain an image via a camera of the endpoint device;
  determine the presence of the triggering object by comparing a sample image of the triggering object to the image obtained via the camera, wherein the image obtained via the camera includes the triggering object; and
  send a notification to the device, when the presence of the triggering object is determined by the endpoint device.

16. A non-transitory computer-readable medium storing instructions which, when executed by a processor in a network, cause the processor to perform operations, the operations comprising:
  receiving a configuration file, the configuration file identifying a triggering object relating to a mental condition of a user, a threshold for detecting a negative mental state of the user, a type of automated alert, and an automated remedial action;
  detecting a presence of the triggering object;
  obtaining a measurement of the user via a physiological sensor in response to the detecting of the presence of the triggering object;
  detecting the negative mental state of the user, when the measurement of the user via the physiological sensor reaches the threshold for detecting the negative mental state of the user;
  sending an alert of the type of automated alert to a monitoring device, in response to detecting the presence of the triggering object, wherein the alert identifies the negative mental state of the user and a location of the user; and
  performing the automated remedial action, in response to the detecting the presence of the triggering object and the detecting the negative mental state of the user based upon the measurement, wherein the automated remedial action comprises presenting a message to the user to avoid the negative mental state of the user.

17. A method comprising:
  receiving, by a processor, a configuration file, the configuration file identifying a triggering object relating to a mental condition of a user, a threshold for detecting a negative mental state of the user, a type of automated alert, and an automated remedial action;
  detecting, by the processor, a presence of the triggering object;
  obtaining, by the processor, a measurement of the user via a physiological sensor in response to the detecting of the presence of the triggering object;
  detecting, by the processor, the negative mental state of the user, when the measurement of the user via the physiological sensor reaches the threshold for detecting the negative mental state of the user;
  sending, by the processor, an alert of the type of automated alert to a monitoring device, in response to detecting the presence of the triggering object, wherein the alert identifies the negative mental state of the user and a location of the user; and
  performing, by the processor, the automated remedial action, in response to the detecting the presence of the triggering object and the detecting the negative mental state of the user based upon the measurement, wherein the automated remedial action comprises presenting a message to the user to avoid the negative mental state of the user.

18. The method of claim 17, wherein the remedial action further comprises:
  sending an additional alert to an emergency response entity.

19. The method of claim 17, wherein the processor comprises a processor of an endpoint device.

20. The method of claim 17, wherein the processor comprises a processor of a device deployed in a cellular network.

* * * * *